United States Patent [19]

Takahashi et al.

[11] 4,247,729
[45] Jan. 27, 1981

[54] PROCESS FOR PRODUCING HIGH PURITY BENZENE

[75] Inventors: Hideyuki Takahashi; Yoshiyuki Matsuoka; Susumu Hamanishi, all of Yokkaichi, Japan

[73] Assignee: Mitsubishi Petrochemical Company, Limited, Tokyo, Japan

[21] Appl. No.: 27,305

[22] Filed: Apr. 5, 1979

[30] Foreign Application Priority Data

Apr. 10, 1978 [JP] Japan .................. 53-41170

[51] Int. Cl.³ .................. C07C 4/12; C07C 7/00
[52] U.S. Cl. .................. 585/483; 585/804; 585/823
[58] Field of Search .................. 585/483, 486, 488, 489, 585/804, 823

[56] References Cited

U.S. PATENT DOCUMENTS

| 3,310,592 | 3/1967 | Fukuda et al. | 585/259 |
| 3,835,037 | 9/1974 | Fairweather et al. | 208/260 |
| 4,024,026 | 5/1977 | Gewartowski | 585/488 |
| 4,053,388 | 10/1977 | Bailey | 585/483 |
| 4,058,452 | 11/1977 | Loboda | 585/489 |

Primary Examiner—Curtis R. Davis
Attorney, Agent, or Firm—Oblon, Fisher, Spivak, McClelland & Maier

[57] ABSTRACT

A liquid product obtained by hydrodealkylation of hydrocarbon oil containing aromatic hydrocarbons is firstly subjected to rectification, then thus obtained substantially pure benzene is treated with clay substance under a temperature below 120° C. A highly purified benzene especially good in color is obtained.

7 Claims, 1 Drawing Figure

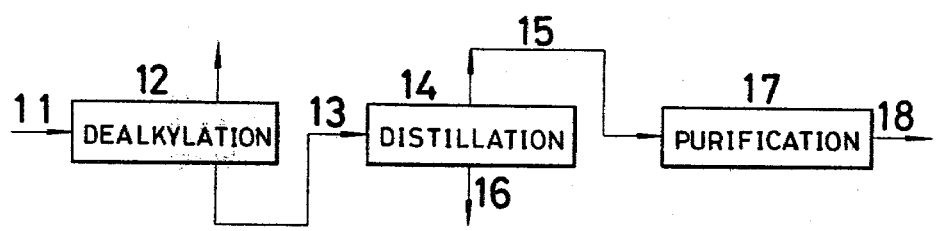

PROCESS FOR PRODUCING HIGH PURITY BENZENE

BACKGROUND OF THE INVENTION

The present invention relates to a process for producing high purity benzene by purifying crude benzene obtained by dealkylation of hydrocarbon fraction containing aromatic hydrocarbon, and more particularly to a process for producing high purity benzene by subjecting the crude benzene fraction obtained in the dealkylation step to a combination of distillation and treatment with an active material.

Various processes are available for obtaining benzene from hydrocarbon fractions containing aromatic hydrocarbons as a raw material. One of the typical process is the so-called extraction process comprising extracting the mixed aromatic hydrocarbons, particularly of benzene, toluene and xylenes by a selective organic solvent, removing the solvent therefrom and fractionating to benzene, toluene and xylenes. Another typical process is the so-called hydrodealkylation process comprising thermally or catalytically hydrodealkylating the similar raw material and increasing a benzene yield, hydrocracking other hydrocarbon than the aromatics to light hydrocarbons, thereby obtaining a liquid phase rich in benzene, and obtaining pure benzene therefrom by distillation. The present invention concerns the latter process.

The light hydrocarbons are removed from the reaction product obtained by the hydrodealkylation process by a stabilizer to obtain a crude benzene fraction. The crude benzene fraction contains aromatic hydrocarbons such as toluene, xylenes, etc. besides benzene, heavier oil, and a very small amount of olefins and thiophenes. Though the olefins and thiophenes are in a very small amount, they remain in the pure benzene even after the distillation, deteriorating the quality of benzene. Thus, it is necessary to remove the olefins and thiophenes by clay treatment.

It is well known that it is desirable to conduct the clay treatment to remove the very small amount of the olefins and thiophenes remaining in the pure benzene freed from the heavier components, thereby obtaining benzene with a higher purity (for example, PETROLEUM REFINER, 42(1963)161). In such a clay treatment, activated clay is chiefly used at a temperature of 150°–230° C. under a pressure of 15–30 kg/cm$^2$. The pressure is applied to keep the benzene in a liquid phase at the treating temperature. The clay treatment has a substantial effect; reduction in the thiophenes and considerable improvements in acid wash color and bromine index of product benzene can be obtained thereby. However, it causes sometimes a development of undesired color in the product benzene. It is a serious problem for the product to meet the standard requirements as a high purity benzene. This is because some heavier oil is formed by the clay treatment, probably due to the polymerization of olefins contained in the benzene. Though the deterioration of color of the high purity benzene by the clay treatment does not always appear, it is actually indispensable to conduct redistillation after the clay treatment to assure the quality in the industrial production. In some processes the clay treatment is carried out before the rectification of benzene, because the redistillation is required after the clay treatment. That is, the crude benzene freed from the light components by a stabilizer in the dealkylation step is subjected to clay treatment, and then pure benzene is obtained by rectification (for example, HYDROCARBON PROCESSING, November (1977),132). However, the heavier oil in the crude benzene is also brought into contact with the clay, thereby promoting the deterioration of the clay and shortening the life of clay.

In the production of pure benzene according to the extraction process, no such problem appears. The crude aromatics obtained according to the extraction process are freed from the light components and the heavy components by distillation, and then resulting mixed aromatics are subjected to clay treatment. Then, rectifications of benzene, toluene and xylenes are carried out and thus the heavy components formed by clay treatment are removed by the successive fractionation as bottoms. In other words, even in the production of pure benzene by extraction process, there exist a distillation step after the clay treatment.

SUMMARY OF THE INVENTION

The present invention provides a process for producing high purity benzene, which comprises a first step in which a hydrocarbon fraction containing aromatic hydrocarbons is subjected to a hydrodealkylation and resulting product is then stabilized by separating a light fraction having a boiling point less than that of benzene, a second step in which the stabilized product is subjected to distillation to obtain a substantially pure benzene containing a very small amount of olefins and thiophenes, and a third step in which the substantially pure benzene is treated with an active material so as to obtain a pure benzene.

BRIEF DESCRIPTION OF THE DRAWINGS

The FIGURE shows the three essential steps of the present invention in which a hydrocarbon raw material is subjected to hydrodealkylation followed by distillation and purification by clay treatment.

DETAILED DESCRIPTION OF THE INVENTION

Any hydrocarbon containing aromatics can be used as a raw material in this invention. They are, for example, by-product cracked gasoline in the naphtha cracking, reformate, a crude toluene fraction for producing benzene by dealkylation of toluene, other by-product oil containing aromatics produced from various petrochemical processes, etc. A boiling range of the raw material is usually from 40° C. to 300° C. The BTX content of the raw material of higher than 50% by weight is preferable from the viewpoint of benzene production efficiency. However, the raw material having lower content of aromatics is also applicable for the hydrodealkylation to produce benzene according to the present invention.

The active materials used in this invention include clay substances (natural clay, acid clay, etc.), derivatives from the clay substances (activated clay, etc.), silica-alumina-containing substances (natural or synthetic zeolite, etc.), or any solid acid substances having similar acid properties.

FIGURE shows the steps of the present invention. Hydrocarbon containing aromatic hydrocarbon is fed to a hydrodealkylation step 12 through 11. In the hydrodealkylation step 12, hydrodealkylation reactions of aromatic hydrocarbons such as toluene, zylenes, etc. take place in the presence of hydrogen. Conditions for the dealkylation reaction are such that, for example, when the raw material oil is a by-product oil (cracked gasoline) of naphtha cracking, it is appropriate that the reaction temperature is 500°–850° C., reaction pressure 10–60 kg/cm² G, and a molar ratio of hydrogen to oil is 2–10. The resulting dealkylated product is such that, in the above case, the benzene content is more than 85% by weight, and further about 0.5% by weight of light gas, about 5% by weight of toluene, xylenes, etc. and 5–6% by weight of tars are contained. The product oil is supplied to a distillation step 14 after the light hydrocarbons has been removed by a stabilizer as a part of the dealkylation step. In the distillation step 14, a benzene fraction is withdrawn through 15, and other aromatic hydrocarbons than benzene are discharged from 16. The distillation step 14 may be comprised of a single distillation column, or may be of such a system as to separate the heavy oil at first, and then separate benzene from other aromatic hydrocarbons. Benzene withdrawn into 15 generally has a purity of higher than 99.99% by weight, but still contains less than about 100 wt. ppm of olefins and a very small amount of thiophenes, and shows a bromine index of about 10, and acid wash color test of No. 4. The bromine index represents the number of milligrams of bromine consumed by 100 g of sample according to ASTM D1491. The benzene is fed to a purification step 17 using an active material. The step 17 is a type of an adsorping column usually packed with active materials shaped in granular forms. The operating conditions of such column are such that a temperature is in a range of the room temperature to 120° C., and any pressure can be applied so long as benzene can be kept in a liquid phase at that temperature, but usually the pressure is 5–20 kg/cm². A liquid hourly space velocity is not critical, either, but usually is 0.1 to 10 vol./vol. hour. These conditions are appropriately selected, depending upon the kind of the active material. Purified benzene substantially freed from the impurities such as olefins, thiophenes, etc, in the purification step 17 is obtained from 18. The product benzene shows the color, solidification point, acid wash color, etc. which each satisfy the ATSM standard requirements of pure benzene.

EXAMPLE

Crude benzene obtained by hydrodealkylation of the by-product cracked gasoline from naphtha cracking was freed from other aromatic hydrocarbon fractions such as toluene, xylenes, etc. by distillation. The resulting product was a substantially pure benzene and passed through the layer of activated clay, Nikkanite G-36 made by Nippon Kasseihakudo Co., Ltd., under the following two conditions. Benzene before the clay treatment shows a bromine index of about 13 and an acid wash color of 4.

Average temperatures of layer: 80° C. and 100° C.
Operating pressure: 20 kg/cm²G
Liquid hourly space velocity of benzene stream: 1.0 hr.$^{-1}$ Purified benzene resulting from the clay treatment shows a bromine index of less than 1, and an acid wash color of less than 1. All other properties including the color satisfied the ASTM standard requirements. The results are given in Table.

COMPARATIVE EXAMPLE

The clay treatment was carried out in the same manner as in Example, except that the average temperature of layer was 170° C. The resulting benzene had a deteriorated color, which did not satisfy the ASTM standard requirements. The results are given together in Table.

TABLE

| | | Feed oil (line 15) | Example Purified benzene (line 18) | | Comp. Example Purified benzene (line 18) |
|---|---|---|---|---|---|
| Operating | Temperature (°C.) | | 100 | 80 | 170 |
| conditions | Pressure (kg/cm²G) | | 20 | 20 | 20 |
| | LHSV (hr$^{-1}$) | | 1 | 1 | 1 |
| Color | | good | good | good | not good |
| Specific gravity (15/4° C.) | | 0.8853 | 0.8845 | 0.8847 | 0.8848 |
| Acid wash color | | No.4 | less than No.1 | less than No.1 | less than No.1 |
| Solidification point (°C.) | | 5.5 | 5.5 | 5.5 | 5.5 |
| Thiophene (mg/l) | | 1.5 | 0.7 | 0.7 | 0.9 |
| Bromine index | | 12.9 | less than 1 | less than 1 | less than 1 |
| Distillation | IBP (°C.) | 80.0 | 79.8 | 79.8 | 79.9 |
| range | 5% | 80.1 | 80.0 | 79.9 | 80.1 |
| | 10% | 80.2 | 80.0 | 79.9 | 80.1 |
| | 90% | 80.2 | 80.1 | 80.1 | 80.1 |
| | 97% | 80.2 | 80.2 | 80.2 | 80.2 |
| | EP | 80.2 | 80.2 | 80.2 | 80.2 |
| | Total distillate (%) | 98.5 | 98.5 | 98.5 | 98.5 |

We claim:
1. A process for producing high purity benzene, comprising:
    (a) hydrodealkylating a hydrocarbon fraction containing aromatic hydrocarbons and stabilizing said hydrodealkylated fraction by separating a light fraction having a boiling point less than that of benzene therefrom;
    (b) distilling said stabilized fraction thereby obtaining a substantially pure benzene fraction which contains a very small amount of olefins and thiophene; and
    (c) treating said substantially pure benzene with an active clay substance at a temperature from room temperature to 120° C. thereby obtaining said high purity benzene product.
2. The process according to claim 1, wherein the active material is a clay substance, a derivative of a clay substance, a silica-alumina containing substance or a solid acid material having a similar acid property.
3. The process according to claim 1 or 2, wherein the operating temperature of step (c) is from room temperature to 120° C., and wherein the pressure is sufficient to maintain benzene in the liquid phase.

4. The process according to claim 1, wherein said hydrocarbon fraction is a by-product cracked gasoline from naphtha cracking, a reformate or a crude toluene fraction.

5. The process of claim 2, wherein said silica-alumina containing substance is a natural or synthetic zeolite.

6. The process of claim 1, wherein said hydrodealkylated hydrocarbon fraction contains more than 85% by weight benzene.

7. The process of claim 1, wherein said substantially pure benzene fraction has a purity greater than 99.99% by wt., contains less than about 100 wt. ppm of olefins, has a bromine index of about 10 and an acid wash color test of No. 4.

* * * * *